United States Patent [19]

van der Jagt

[11] Patent Number: Plant 5,781

[45] Date of Patent: Aug. 12, 1986

[54] CHRYSANTHEMUM REEF

[75] Inventor: Martinus van der Jagt, Ter Aar, Netherlands

[73] Assignee: Chrysanthemum Breeders Association N.V., Netherlands Antilles

[21] Appl. No.: 599,701

[22] Filed: Apr. 12, 1984

[51] Int. Cl.[4] ..... A01H 5/00

[52] U.S. Cl. ..... Plt./76

[58] Field of Search ..... Plt./76

*Primary Examiner*—Robert E. Bagwill

*Attorney, Agent, or Firm*—Parkhurst & Oliff

[57] ABSTRACT

The present invention is a new and distinct variety of chrysanthemum of medium size bloom and a phlox purple color.

3 Drawing Figures

BACKGROUND OF THE INVENTION

The present invention comprises a new and distinct cultivar of chrysanthemum plant which is a cross of unknown parents. The invention was discovered by Martinus van der Jagt in May 1982 at Paradysweg 88, Ter Aar, Holland. The invention has been asexually reproduced by cuttings at the same location. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
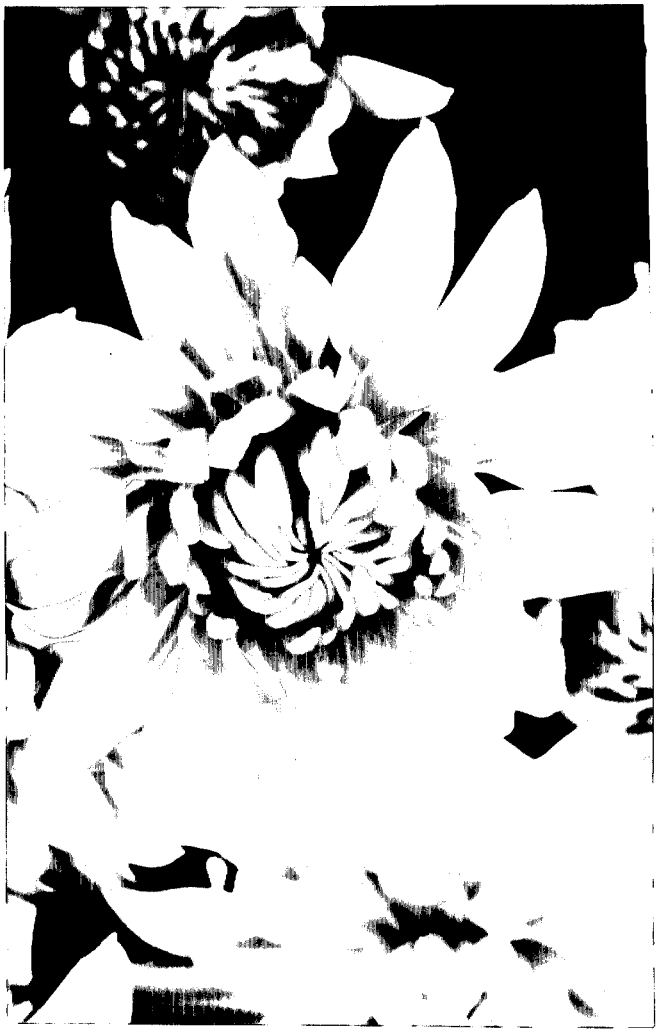
FIG. 1 shows the full bloom of the new cultivar.
Figure 2:
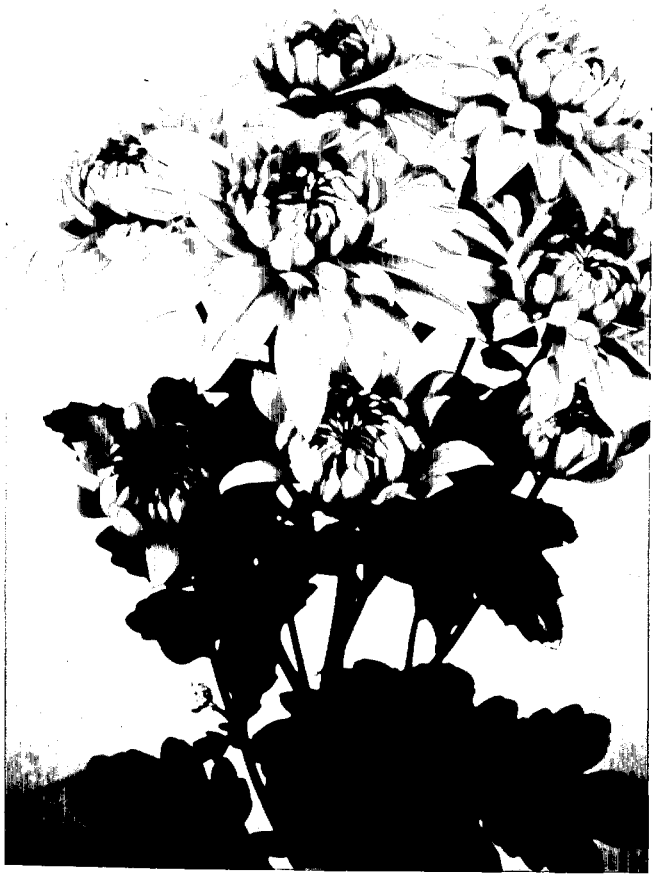
FIG. 2 shows various stages of bloom of the new cultivar.
Figure 3:
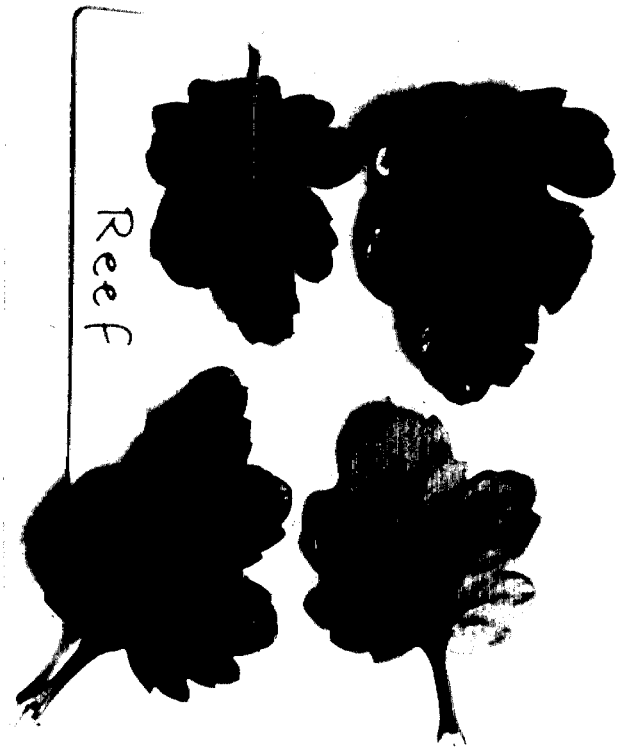
FIG. 3 shows the foliage and stem of the new cultivar.

This new variety of chrysanthemum is of the botanical classification *Chrysanthemum morifolium*. When grown in the vicinity of, Ter Aar, Holland, it has a response time of approximately 9½ weeks. This new variety produces medium sized phlox purple blooms with a violet center having a 2½ weeks permanence. This new variety of chrysanthemum has been found to retain its distinctive characteristics throughout successive propagations and may be grown year round under greenhouse conditions.

The following is a description of the plant and characteristics that distinguish it over related known variety and its anticedents:

Bud:
- *Size.*—Big.
- *Form.*—Flat.
- *Color.*—Pink when petals first divide, violet when petals begin to unfurl (R.H.S. 632).

Botanical classification: *Chrysanthemum morifolium.*

Bloom:
- *Size.*—Medium.
- *Fully.*—7–8 cm.
- *Borne.*—Single.
- *Stems.*—Strong.
- *Form.*—Decorative.
- *Permanence.*—18 Days.

Color:

- *Center of flower.*—Phlox purple R.H.S. 632/1.
- *Base of petals.*—Phlox purple (R.H.S. 632/1).
- *Inside of petals.*—Phlox purple to pink (R.H.S. 632/1).
- *Reverse of petals.*—Pink (R.H.S. 632/3).
- *Outer petals.*—Pink (R.H.S. 632/3).
- *Tonality from a distance.*—Classical decorative flower with a phlox purple color fading to pink to the end.
- *Discoloration.*—Yes, to pastel pink/phlox purple (R.H.S. 632/2).

Petals:
- *Texture.*—Decorative form, incurving petals.
- *Number.*—Appr. 50–70 besides the unfurling petals in the center.
- *Arrangement.*—Imbricated.
- *Persistence.*—Normal.
- *Fragrance.*—Chrysanthemum.

Reproductive organs:
- *Stamen.*—Very small.
- *Pollen.*—None to few.
- *Styles.*—Columnar.
- *Length.*—Short.
- *Stigmas.*—Very small.
- *Ovaries.*—Enclosed in calyx.

Plant:
- *Form.*—Herbaceous.
- *Growth.*—Strong.
- *Height.*—Tall.
- *Pendundle.*—Strong.

Foilage:
- *Color.*—Normal.
- *Size.*—Normal.
- *Quantity.*—Normal.
- *Shape.*—Round.
- *Texture.*—Hard, leathery.
- *Ribs and veins.*—Not conspicious.
- *Edge.*—Undulated.
- *Leaf underside.*—Smooth.

In the description above color references are made to the "Horticultural Colour Chart I & II" issued by the British Colour Council in collaboration with The Royal Horticultural Society, Copyright Robert F. Wilson, Vol. I, 1938; Vol. II, 1941, printed by Henry Stone and Son, Ltd. Banbury, England.

I claim:

1. A new and distinctive variety of chrysanthemum as described and illustrated in the foregoing specification and accompanying drawings.

* * * * *